United States Patent
Larrabide (10) Patent No.: US 10,176,566 B2
(45) Date of Patent: Jan. 8, 2019

(54) METHOD FOR DETERMINING THE FINAL LENGTH OF STENTS BEFORE THE POSITIONING THEREOF

(71) Applicant: GALGO MEDICAL, S.L., Barcelona (ES)

(72) Inventor: Ignacio Larrabide, Barcelona (ES)

(\*) Notice: Subject to any disclaimer, the term of this patent is extended or adjusted under 35 U.S.C. 154(b) by 249 days.

(21) Appl. No.: 14/911,938

(22) PCT Filed: Oct. 3, 2014

(86) PCT No.: PCT/ES2014/070758
§ 371 (c)(1),
(2) Date: Feb. 12, 2016

(87) PCT Pub. No.: WO2015/063352
PCT Pub. Date: May 7, 2015

(65) Prior Publication Data
US 2016/0232659 A1    Aug. 11, 2016

(30) Foreign Application Priority Data
Oct. 31, 2013 (ES) .................. 201331605

(51) Int. Cl.
*G06F 7/60* (2006.01)
*G06F 17/10* (2006.01)
(Continued)

(52) U.S. Cl.
CPC .............. *G06T 7/0012* (2013.01); *A61B 6/12* (2013.01); *A61B 8/0841* (2013.01); *A61B 34/10* (2016.02); *A61F 2/82* (2013.01); *G01N 15/088* (2013.01); *G06F 19/00* (2013.01); *G06T 7/60* (2013.01); *G16H 50/50* (2018.01); *A61B 5/20* (2013.01); *A61B 5/6862* (2013.01); *A61B 2034/102* (2016.02); *A61B 2034/108* (2016.02);
(Continued)

(58) Field of Classification Search
None
See application file for complete search history.

(56) References Cited

U.S. PATENT DOCUMENTS

2011/0071404 A1\* 3/2011 Schmitt ................ A61B 5/0066
600/479
2014/0100442 A1\* 4/2014 Begin .................... A61B 8/466
600/411

FOREIGN PATENT DOCUMENTS

| DE | 102012217268 A1 | 9/2013 |
|----|-----------------|--------|
| JP | 2001-079097 A | 3/2001 |
| WO | 2008/041154 A2 | 4/2008 |
| WO | 2011/121516 A2 | 10/2011 |
| WO | 2012/170448 A1 | 12/2012 |

OTHER PUBLICATIONS

Larrabide, Ignacio et al. "Three-Dimensional Morphological Analysis of Intracranial Aneurysms: A Fully Automated Method for Aneurysm Sac Isolation and Quantification", May 2011, Med. Phys. 38 (5), Am. Assoc. Phys. Med. (Year: 2011).\*

(Continued)

*Primary Examiner* — Cedric Johnson
(74) *Attorney, Agent, or Firm* — Eugenio J. Torres-Oyola; Victor M. Rodriguez-Reyes; Ferraiuoli LLC (57) ABSTRACT

The invention relates to a new method for determining the change in length of a stent which will occur after it has been implanted inside a vascular structure. Said determining process is carried out based on the relationship between said change in length and the morphological characteristics of the vascular structure of interest.

5 Claims, 9 Drawing Sheets

(51) Int. Cl.
  *G06T 7/00* (2017.01)
  *A61B 6/12* (2006.01)
  *A61B 8/08* (2006.01)
  *A61B 34/10* (2016.01)
  *G01N 15/08* (2006.01)
  *A61F 2/82* (2013.01)
  *G06T 7/60* (2017.01)
  *G16H 50/50* (2018.01)
  *G06F 19/00* (2018.01)
  *G06F 17/50* (2006.01)
  *A61B 5/00* (2006.01)
  *A61F 2/86* (2013.01)
  *A61B 5/20* (2006.01)

(52) U.S. Cl.
  CPC ........... *A61F 2/86* (2013.01); *A61F 2240/002* (2013.01); *G06F 17/50* (2013.01); *G06T 2200/04* (2013.01)

(56) References Cited

OTHER PUBLICATIONS

Larrabide, Ignacio et al., "Fast Virtual Deployment of Self-Expandable Stents: Method and In Vitro Evaluation for Intracranial Aneurysm Stenting", May 11, 2010, Medical Image Analysis, Elsevier B.V. (Year: 2010).*

Morlacchi, S, et al., Patient-specific simulations of stenting prodecures in coronary bifurcations: two clinical cases, Medical Engineering & Physics, Sep. 2013, vol. 35, No. 9, pp. 1272-1281.

Larrabide, I, et al., Fast virtual deployment of self-expandable stents: Method an in vitro evaluation for intracranial aneurysmal stenting, Medical Image Analysis, Apr. 2012, vol. 16, No. 3, pp. 721-730.

Extended European Search Report dated Apr. 18, 2017 in corresponding ES Application No. 14859121.7.

* cited by examiner

METHOD FOR DETERMINING THE FINAL LENGTH OF STENTS BEFORE THE POSITIONING THEREOF

CROSS-REFERENCE TO RELATED APPLICATIONS

This application is the U.S. National Phase under 35. U.S.C. § 371 of International Application PCT/ES2014/070758, filed Oct. 3, 2014, which claims priority to Spanish Patent Application No. 201331605, filed Oct. 31, 2013. The disclosures of the above-described applications are hereby incorporated by reference in their entirety.

FIELD OF THE INVENTION

The present invention refers to a new method for determining the change in length of a stent which will occur after it has been implanted inside a vascular structure. Said determination is carried out on the basis of the relationship of said change in length with the morphological characteristics of the vascular structure of interest.

BACKGROUND OF THE INVENTION

In general, the term stent is a medical Anglicism in common use to designate a cannula or device of a cylindrical or tubular shape for intraluminal, usually intravascular, use, which is placed inside an anatomical structure or bodily duct in order to keep it permeable or prevent its collapse after dilation, clearing or surgical release. A stent is typically implanted in a blood vessel at the site of a stenosis or intraluminal aneurysm, i.e. using so-called "minimally invasive techniques", in which the stent is contained in a radially compressed configuration by a sheath or catheter and is delivered using a stent application device or "inserter" into the required site. The inserter may enter the body from a place of access outside the body, such as through the patient's skin or using a technique of incision in which the blood vessel of entry is exposed to minor surgical equipment.

As used in this document, the term stent also refers to grafts, stent-grafts, vena cava filters, expandable structures and similar implantable medical devices, which are radially expandable endoprostheses. Usually they are intravascular implants capable of being implanted transluminally and they are enlarged radially after being inserted percutaneously.

Stents can be implanted in various lumina or vessels in the body, such as in the vascular system, the urinary tract, and bile ducts, among others. Said stents can be used to reinforce blood vessels and prevent restenosis following angioplasty in the vascular system. Stents may be self-expanding, such as nitinol shape memory stents; also they may be mechanically expandable, such as a balloon-expandable stent; or they may be hybrid expandable.

The use of intraluminal stents is very common in various areas of medicine and veterinary practice. There are various designs of stents for intraluminal insertion into blood vessels and other lumina to prevent or reverse their occlusion. In general, three basic categories of stent-type devices are considered to exist, as follows:
  heat-expandable devices,
  balloon-expandable devices, and
  self-expanding devices.

The present invention refers to self-expanding stent-type devices which, optionally, have the ability to expand by heat, which are inserted into a vessel within the body in a radially compressed form and mechanically change to a radially expanded form. Once the stent is placed in the desired position in the blood vessel, it expands radially, exerting outwards pressure on the internal surface of the wall of the body vessel in which it has been positioned.

Braided stents are manufactured by braiding (interweaving) wires of a thin metallic material according to different braiding patterns. U.S. Pat. No. 6,083,257A describes a method for braiding stents. According to the number of wires, the braiding angle, the nominal radius, the nominal length, and the braiding pattern used, the mechanical properties and density of the resulting stent mesh may vary considerably. The present invention covers both braided and unbraided stents.

In the present document, the term "nominal radius" refers to the radius adopted by the stent when it is left freely outside a vessel or the positioning device and it coincides with the maximum radius when it is released outside the vessel.

In the present document, the term "nominal length" refers to the length adopted by the stent when it is left freely outside a vessel or the positioning device. Therefore, the stent adopts the "nominal length" when it possesses its "nominal radius".

Stents are often used for the treatment of intracranial aneurysms (IA), a sector in which there are various types of braided stents. One of these types is known as a "Flow Diverter" (FD, its initials in English), it is densely braided and is placed longitudinally along the vessel affected by the aneurysm, and covers the neck of the aneurysm. Alternatively, coarse braided stents are also used as a scaffolding for the protection of the neck of the IA after the positioning of an intravascular coil, as is made known in U.S. Pat. No. 6,010,468A.

Stents are positioned in the desired place using a catheter, in image-guided operations, typically with an interventional X-ray image, with the aid of a contrast marker which shows the location of the vessel lumen and, where appropriate, the aneurysm to be treated. In the case of aneurysms, the catheter is inserted into the body normally through arteries, for example the iliac artery, and is guided to the location of the aneurysm by a neurointerventional radiologist. Said radiologist will select the position at which the distal end of the stent is placed and will gradually unsheathe the stent until it is fully released in the vessel being treated.

Nevertheless, stents present the difficulty that the final length of the stent when it is positioned inside the body is not accurately known in advance and is difficult to predict with the naked eye.

Usually, the estimation of the final length of a stent when placed inside a vessel is made with the naked eye and the stent is assumed to be released in a straight vessel of constant radius. This method provides very poor references in relation to the final length the stent will have in the patient, as most of the vessels are neither straight nor do they have a constant radius.

When a stent is released outside the human body, as mentioned previously, it adopts its nominal radius. However, if this stent is placed inside a vessel with a radius smaller than its nominal radius, the vessel walls prevent the full expansion of the stent and this forces the device to present a configuration with greater length. The fact that the change in the total length of the stent depends on the morphology of the vessel makes it very difficult to predict the final length of said device, prior to its positioning. As the medical practitioner is unable to predict accurately the final length of the stent placed inside the patient, it may happen that collateral branches of the vessel being treated become obstructed or occluded, and this may cause injury to the patient. Furthermore, in the case of intracranial aneurysms, variation in the density of the stent mesh as a result of the various degrees of expansion makes the effect of the device on the blood flow inside the aneurysm difficult to predict. These potentially adverse effects of the treatment mean that it is necessary to create a tool which makes it possible to predict accurately the final length and configuration of the stent, once placed at a particular position inside the lumen of a vascular structure in the body.

There are antecedents which describe methods for modelling stents. Deformable models have been used to simulate the behaviour of a stent when it is positioned inside the lumen of a vessel (Larrabide, I. et al. "Fast virtual deployment of self-expandable stents: method and in vitro evaluation for intracranial aneurysmal stenting", Medical Image Analysis, 2012, 16(3), 721-730). However, said method does not allow the change in length of the stent to be predicted, as it takes no account of its mechanical behaviour.

Other methods based on mechanical deformation of a structure similar to a cylinder have also been proposed (Cebral, J. R. and Lohner, R. "Efficient simulation of blood flow past complex endovascular devices using an adaptive embedding technique" IEEE Transactions on Medical Imaging, 2005, 24(4), 468-476), but they are not able to predict the change in the length of the stent either.

Recently, a method has been disclosed based on the use of finite elements and a detailed description of the braiding pattern, which allows more accurate modelling of the mechanical behaviour of the stent-type device (Ma, D. et al. "Computer modelling of deployment and mechanical expansion of neurovascular flow diverter in patient-specific intracranial aneurysms" Journal of Biomechanics, 2012, 1-8). This method provides considerable accuracy when it comes to modelling the behaviour of a stent, however, the obtainment of the models is extremely complex and long.

Other methods based on the obtainment of images of lumina of the vessels to be treated and modelling for the determination of the most appropriate stent are made known in International Patent Applications WO2006/093776 and WO2011/038044 and United States Patent Application US2007/0135707.

International Patent Application WO2006/093776 discloses a procedure for modelling stents based on the use of an ultrasound imaging system for obtaining images of blood vessels, detecting defects in said vessels and using said images to perform graphic simulations with various stents to check whether the length and position are appropriate. International Patent Application WO2011/038044, for its part, discloses an automated procedure for simulating the length and position of stents based on the obtainment of images of the lumen of the blood vessel by means of optical coherence tomography. From the images obtained, a three-dimensional reconstruction is made of the contours of the vessel lumen, data are obtained relating to the diameter of the vessel and the blood flow rate, pressure and resistance in order finally to simulate and optimise the length and/or position of the stent.

Lastly, United States Patent Application US2007/0135707 discloses the obtainment of three-dimensional images with which a model of the vessel to be treated can be constructed in order to detect the lesion and its characteristics and simulate the stent to be used and the position at which it will be placed.

SUMMARY OF THE INVENTION

The present inventors have developed a method for determining, before its positioning, the final length a stent will have after it is placed in a vascular structure. Said method makes it possible to determine, prior to its implantation and with a high degree of accuracy, the final length of a stent on the basis of the initial position in which it is placed in said vascular structure.

The method of this invention is based on an analysis of the local morphology of the vascular structure in which said stent will be placed and an analysis of the change in length of this, and it requires the definition and use of a ratio indicating the change in length of the stent as a function of the local morphology of the vessel and the place where it is intended to place the device.

Therefore, the method for determining the final length of a stent before it is positioned in a vascular structure according to the present invention consists of the following steps:
  a) determine the ratio indicating the change in length of the stent as a function of the local morphology of the vascular structure;
  b) obtain the three-dimensional centreline of the vascular structure in which the stent will be placed;
  c) define the exact location of the starting point at which said stent will be placed in said vascular structure;
  d) divide said centreline of the vascular structure obtained in step b) into small segments;
  e) determine the descriptive parameters of the morphology of said vascular structure for the first segment which starts from said initial point at which said stent will be placed in said vascular structure;
  f) calculate the length of the stent for said first segment using the indicator ratio of step a);
  g) subtract said length of the segment calculated in step f) from the nominal length of the stent in order to obtain a new nominal length; if said new nominal length is different from 0 then steps e) to g) will be repeated for the segment contiguous with the preceding segment; if the new nominal length is approximately 0, all the distances of each segment will be added together, and this sum will be the final length of said stent after its positioning.

The method of the present invention may be applied to any type of braided or unbraided stent, provided that the length of said stent changes when its diameter varies.

The determination of the indicator ratio of the change in length of the stent as a function of the local morphology of the vascular structure of step a) of the method of the present invention is specific to each type of stent to be used. In this ratio different morphological descriptors of vascular structures are used such as the average radius (average distance from the centreline to the points on the cross section of the vascular structure at that point of the centreline), maximum inscribed sphere radius (MISR, initials in English, minimum distance from the centreline to the surface of the vascular structure), cross sectional area (cross sectional area at a point on the centreline), perimeter of the cross section (length of the curve obtained by cutting a cross section of the vascular structure), minimum radius of the cross section, maximum radius of the cross section, and curvature/torsion, among others. For each device to be used, a specific function must be provided which relates said morphological descriptors with the change in length of the stent.

In the method of the present invention, the vascular structure in which the stent will be positioned must be provided in the form of a three-dimensional surface. Said three-dimensional surface of the vascular structure may be obtained by any method known in the art, for example, by image segmentation of an angiographic image (Hernández, M. and Frangi, A. F. "Non-parametric geodesic active regions: method and evaluation for cerebral aneurysms segmentation in 3DRA and CTA" Medical Image Analysis, 2007, 11(3), 224-241; and Antigua, L. et al. "An image-based modeling framework for patient-specific computational hemodynamics" Medical and Biological Engineering and Computing, 2008, 46(11), 1097-1112) and subsequent reconstruction of the surface (Lorensen, W. E. and Cline, H. E. "Marching Cubes: A high resolution 3D surface construction algorithm" Computer Graphics, 1987, 21, 4). The three-dimensional surface of the vascular structure can be represented by means of a polygonal mesh, in which the resolution can be adjusted in order to obtain relevant information on the morphology of the vascular structure. As mentioned previously, these techniques are known in the art, and any other known technique may be used provided that it allows a three-dimensional surface of the vascular structure in which the stent will be positioned to be obtained.

With the method of the present invention, it is not only possible to predict, before its positioning, the final length of a stent when it is positioned inside a vessel, but it is also possible to detect regions in which there could be poor apposition of the stent to the walls of the vascular structure, occlusion or total or partial covering of ramified vessels and the porosity or density resulting from the stent.

The use of the method of the present invention makes it possible for a neurointerventional radiologist, for example, to plan the treatment and ascertain the final disposition of the stent before the said treatment is carried out and therefore this will enable him to select the optimal stent and the exact location at which said stent will be positioned.

Furthermore, the method of the present invention can be implemented by means of a computer program which would allow said determination of the final length of the stent to be carried out with greater speed and accuracy. For example, optionally step d) may be carried out continuously instead of performing the discretisation of the centreline of the vascular structure.

Occasionally, the indicator ratio of the change in length of the stent of step a) of the procedure of this invention is given by the manufacturer of said stent. Therefore, it is not necessary to carry out step a). For this specific embodiment, the method for determining the final length of a stent of the present invention comprises the following steps:
  a) obtain the three-dimensional centreline of the vascular structure in which the stent will be positioned;
  b) define the exact location of the starting point at which the stent will be positioned in said vascular structure;
  c) divide said centreline of the vascular structure obtained in step b) into small segments;
  d) determine the descriptor parameters of the morphology of said vascular structure for the first segment which starts out from said starting point at which said stent will be positioned in said vascular structure;
  e) calculate the length of the stent for said first segment using the indicator ratio given by the manufacturer of said stent;
  f) subtract said segment length calculated in step e) from the nominal length of the stent in order to obtain a new nominal length; if said new nominal length is different from 0 then steps d) to f) will be repeated for the segment contiguous with the preceding segment; if the new nominal length is approximately 0, all the distances of each segment will be added together, and this sum will be the final length of said stent after it is positioned.

BRIEF DESCRIPTION OF THE DRAWINGS

For a better understanding, the present invention is described below with reference to the enclosed figures, which are presented by way of example, and in no case are intended to be by way of limitation of the present invention.

FIG. 7a) shows the cross section of a vessel and FIGS. 7b) and c) show two different stents positioned in the same lesion.

DETAILED DESCRIPTION OF THE PREFERRED EMBODIMENTS

Figure 1:
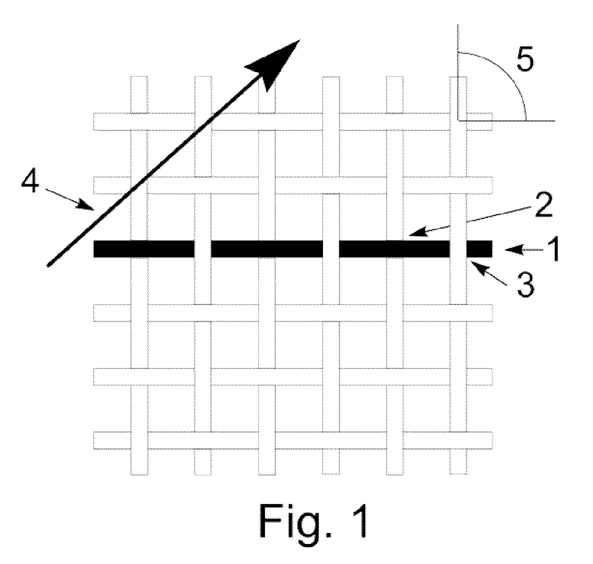
FIG. 1 shows a detail of a side view of a possible interweave pattern of a braided-type stent.

FIG. 1 shows an interweave pattern of a braided stent known in the art, in which a wire -1- is highlighted and it is shown how said wire -1- crosses in front -2- and behind -3- other wires. FIG. 1 also shows the braiding angle -5- and the direction of braiding -4-.

Figure 2:
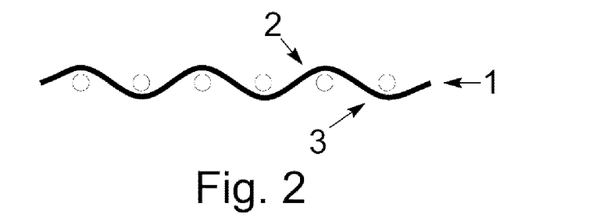
FIG. 2 shows a detail of a cross section following the direction of a wire of the braided stent of FIG. 1.

FIG. 2 shows a front view of the interweave pattern shown in FIG. 1. It is also observed how the marked wire -1- crosses over -2- and under -3- other wires which form said stent.

Figure 3:
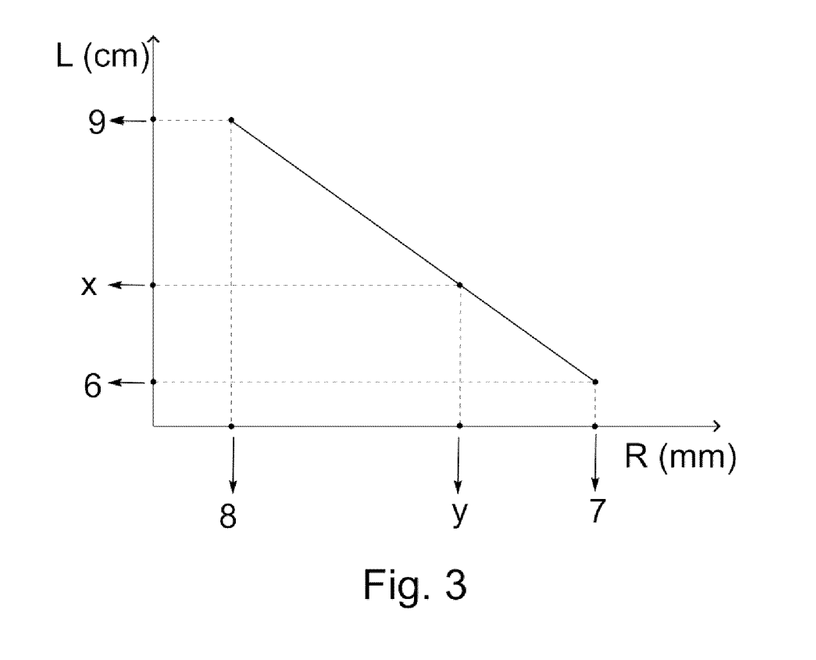
FIG. 3 shows an example of a linear ratio between the change in length of the stent (y axis) and the radius of the cross section of the vascular structure (x axis).

FIG. 3 shows a graph which represents an example of a linear ratio between the change in length of the stent and the radius of the tube or vessel. Furthermore, the following are indicated in the graph: the nominal length -6- of the stent, the nominal radius -7- of the stent, the constrained radius -8- of the stent, the constrained length -9- of the stent and the interpolation of an intermediate radius -y- to obtain the change in length -x-

Figure 4:
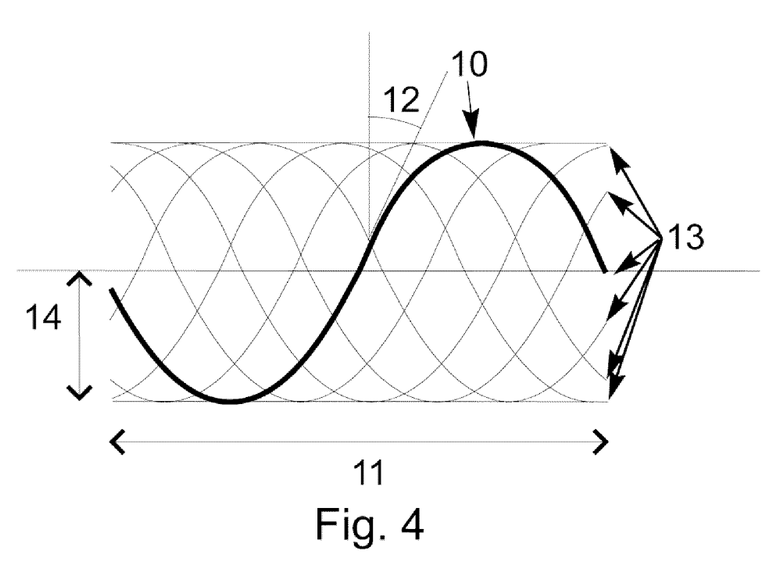
FIG. 4 shows the helicoidal path followed by the wires in a braided-type stent.

FIG. 4 shows the helicoidal distribution of the wires of a braided stent, including the path of a wire marked -10-, the length of the device -11-, the braiding angle -12-, the number of wires -13- and the radius -14-.

Figure 5:
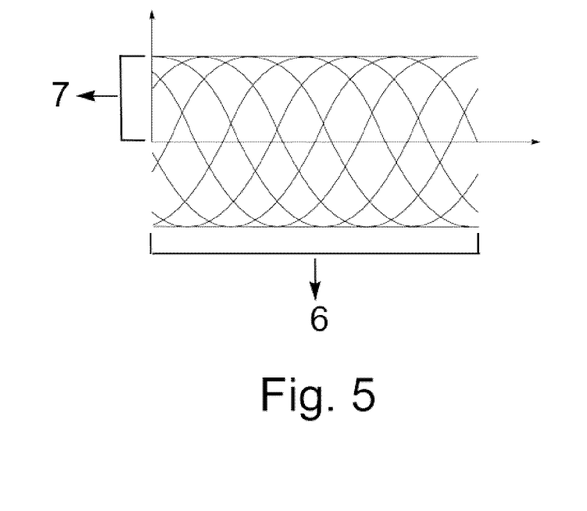
FIG. 5 shows a released, expanded and unconstrained stent.

FIG. 5 shows a braided stent in the expanded and unconstrained state and both the nominal length -6- and the nominal radius -7- are indicated.

Figure 6:
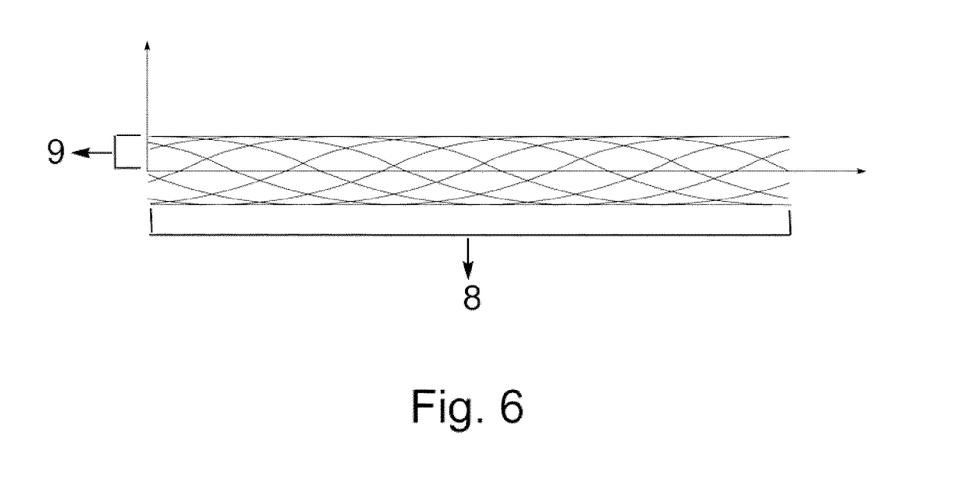
FIG. 6 shows a stent in the unexpanded and constrained state.

FIG. 6 shows a braided stent in the constrained state and the constrained radius -8- and the constrained length -9- may be observed.

Figure 7:
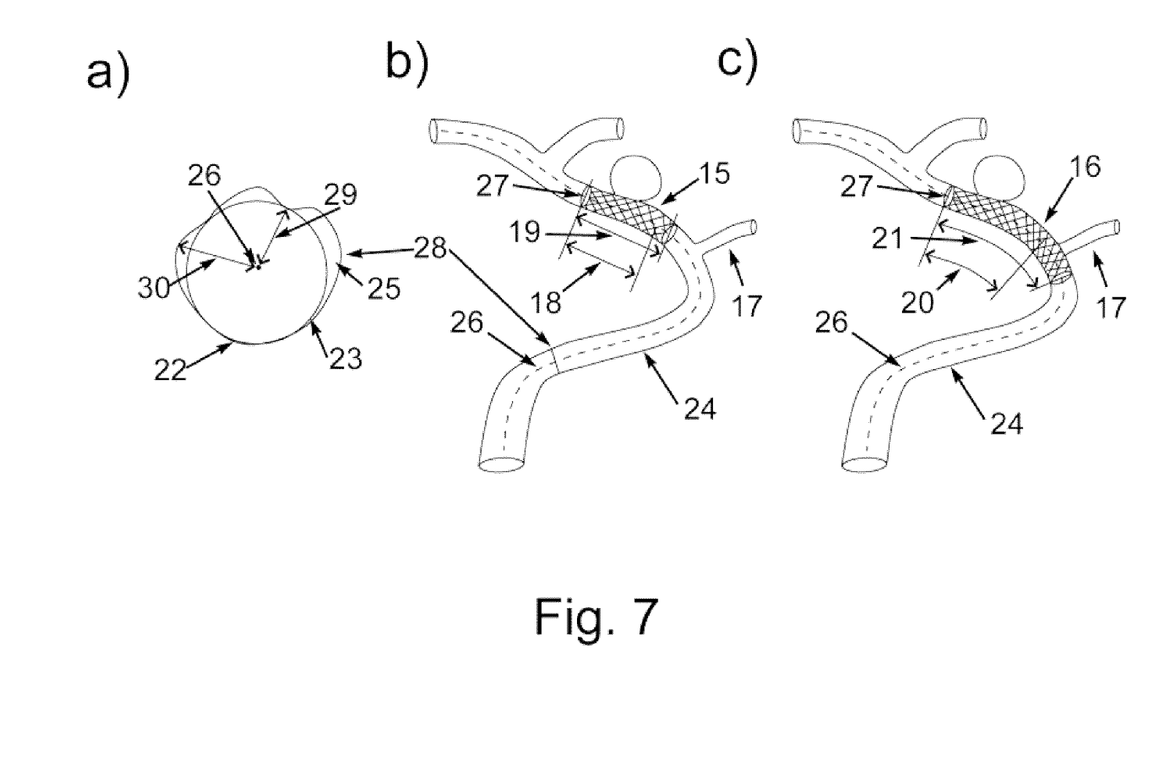

In FIG. 7a) the cross section of a vessel is observed, in which the following may be distinguished: the centreline of the vessel -26-, the minimum radius of the cross section of the vessel -29-, the maximum radius of the cross section of the vessel -30-, the cross sectional area of the vessel -31-, the perimeter of the cross section of the vessel -32- and the maximum inscribed sphere radius of the vessel -33- (the minimum distance from the centreline to the surface of the vascular structure). FIGS. 7b) and c) show different stents positioned in the same initial position of the same vessel and detail the fact of using a short -15- or long -16- device in a vessel-type structure -24-, the presence of ramified vessels -17-, the nominal lengths -18- and -20-, the final lengths -19- and -21-, the centreline of the vessel -26- and the initial position for positioning the stent -27-.

Figure 8:
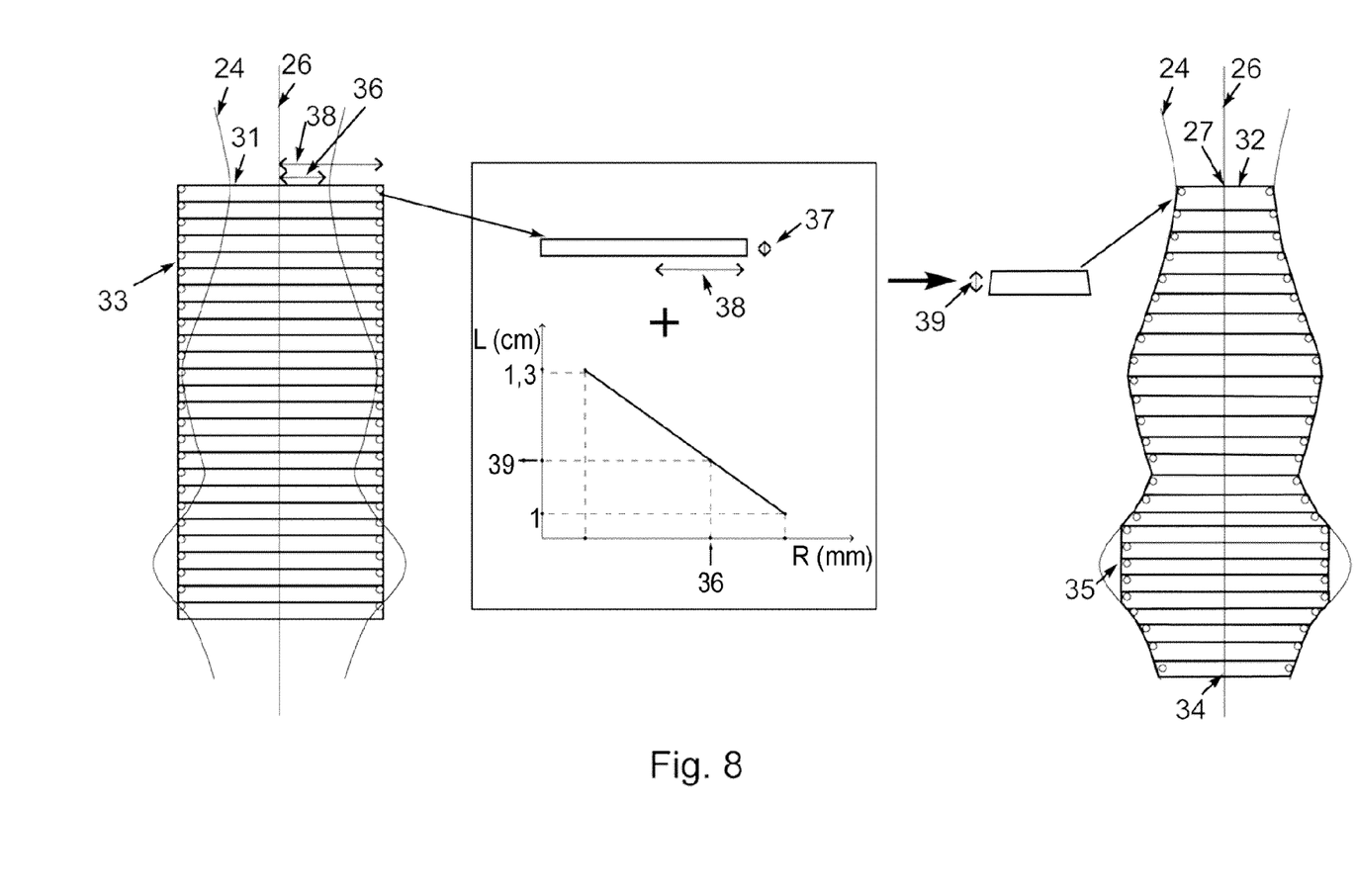
FIG. 8 shows the superimposition of a braided stent on the vessel and its adaptation to the contour of this.

FIG. 8 shows the superimposition of the braided stent on the vessel and, after performing the interpolation, the adaptation of the stent to the morphology of the vessel -24-. In this figure a braided stent in the unconstrained state -22- and a braided stent in the constrained state -23- appear. One may also observe the various sections -25- into which the stent is divided according to the method of the present invention, of which the following are detailed: its nominal length -37- and its nominal radius -38- and the length presented in its constrained form -39-. In the figure one may also distinguish the centreline of the vessel -26-, the initial position where the stent is placed -27-, the final position of the stent after positioning -34- and regions of partial union between the vessel and the stent -35-.

In the present document, the terms "vascular structure", "vessel", "vessels" refer to arteries, arterioles, veins, the intestine, rectum and any other structure of a tubular type present in the human or animal body which is susceptible of treatment with stents.

In the present document, the terms "stent", "stent-type device" refer to braided, unbraided and equivalent stents. Furthermore, the method of the present invention covers both constant radius (cylindrical) stents and non-constant radius stents (conical, combinations of conical/cylindrical, among others).

The determination of the indicator ratio of the change in length of the stent as a function of the local morphology of the vascular structure of step a) of the method of the present invention may be performed experimentally or by means of a mathematical model. In the experimental form phantoms of different diameters are used (with a constant radius in the longitudinal direction) which mimic the vessels in which the stent in question will be positioned and the changes in length per unit length of the stent are measured in order to create a table of values. Furthermore, in the mathematical modelling, as may be observed in FIG. 4, when the length of the wires -10-, the number of wires -13- and the various radii of interest are known, the resulting change in the length of the stent is simulated by modelling the length of the wire as a spiral.

This indicator ratio of the change in length of the stent is designed to provide the change in length of the stent-type device given the local morphology of the vessel. For example, one may obtain the length in the constrained state -8- with respect to the nominal length -6- of the stent when it is placed in tubes of different morphologies (FIG. 3). This change in length can be expressed per unit length, that is to say, the new length of a portion of the instrument of unit length once positioned -9-.

Furthermore, one may also obtain a model which takes account of the change in length with respect to the nominal radius of the stent when it is positioned in tubes with a different morphology in their cross sections. For each stent to be modelled, one must know the relationship between the morphology of the vessel and the change in length of the stent (FIG. 3) and, therefore, a function must be provided which expresses the length for different degrees of expansion. As in the previous case, the change in length can be expressed per unit length, that is to say, the new length of a portion of stent of unit length once positioned -9-.

After obtaining a sufficiently large set of combinations of local morphology of the vessel with respect to the change in length of the stent, a continuous function is created so that the associated change in length can be obtained from the local morphology of the vessel. To be large enough, a set such as that mentioned above must be able to capture any linear or non-linear behaviour of the change in length of the stent. In the case where said behaviour is linear in relation to the morphology, two measurements should suffice (FIG. 3). In this last case, to obtain the change in length of a portion of stent and a local morphology which has not been tested -8-, (FIG. 3), but which are within the range of the conditions tested -26- and -7- in FIG. 3, data interpolation is used. Said interpolation can be performed by using any parametric function (linear, polynomial, among others). The resulting angle between the wires which cross each other should also be measured, thus making it possible to estimate the resulting angle of the wires in the length of the stent. Validation may be carried out by using the same data obtained experimentally to create the function.

The consideration of oversizing the stent in the function mentioned above may require additional experimentation, possibly considering different degrees of oversizing. As a result of oversizing, the stent will present a more obtuse angle between the wires as said oversizing increases, with lower effective porosity, without affecting the nominal radius of the stent. This effect may be considered by the proposed model indicating at which point or zone of the stent the oversizing is obtained and the degree of this (from 0 to 100%). The maximum oversizing of the device must be tested experimentally. All this information is stored and relates the degree of oversizing with the change in length.

In addition, the indicator ratio of the change in length of the stent may take account of geometric considerations related with different curvatures and torsions. For this, one option is to test whether the length of the stent changes when it is implanted in a curved tube compared with a tube of the same radius but with no curvature, that is, straight.

For each of the radii of expansion considered by the indicator ratio, one may also measure the associated angle of interweave for an angle determined experimentally or from an appropriate model. Said angle may be obtained for each radius by interpolation from the data obtained experimentally and the information may be used to model the angle of local interweave. In the case where the change in length is obtained by expansion of the device to different radii, the angle of interweave of the wires may be measured for each expansion and said information may be used in said indicator ratio of the change in length of the stent.

Once the indicator ratio of the change in length of the stent has been obtained in step a) of the method of the present invention, a three-dimensional image of the vascular structure in which the stent will be positioned will be obtained. Said image is nothing more than a three-dimensional representation of said vascular structure and may be obtained by any of the methods known in the state of the art, such as those mentioned previously.

From said image it is possible, using any digital image processor known in the art, to trace a centreline in the three-dimensional representation of said vascular structure in which said stent will be positioned. Furthermore, it is possible to obtain the descriptors of the local morphology of the vascular structure for each point situated on said centreline of the vessel. For example, the centreline of the vessel described in step b) may be obtained by skeletonisation. In the state of the art several methods of skeletonisation are known (Mellado, X. et al. "Flux driven medial curve extraction" The Insight Journal, 2007).

For the division of said centreline of the vascular structure into small segments, which corresponds to step c) of the method of the present invention, various methods may be used for segmentation, whether based on thresholding, image intensity, the growth of regions or sets of levels (Hernández, M. and Frangi, A. F. "Non-parametric geodesic active regions; method and evaluation for cerebral aneurysms segmentation in 3DRA and CTA" Medical Image Analysis, 2007, 11(3), 224-241; and Antigua, L. et al. "An image-based modeling framework for patient-specific computational hemodynamics" Medical and Biological Engineering and Computing, 2008, 46(11), 1097-1112).

Said centreline may be obtained from the structure of the vessel and consists of a single line corresponding to the centreline of a branch of a tree or graph of more complex vessels.

Furthermore, said descriptors of the local morphology of the vascular structure may be the maximum inscribed sphere radius (MISR, initials in English) of the vessel (33), cross section of the vessel (28), area of the cross section of the vessel (31), perimeter of the cross section of the vessel (32), minimum radius of the cross section of the vessel (29), maximum radius of the cross section of the vessel (30) or any combination of these. An expert in the field will understand that it is possible to use other descriptor parameters of the local morphology of the vascular structure in which the stent will be positioned, provided that these affect its final length after positioning.

In the state of the art several methods are known for obtaining the descriptors of the local morphology of vessels (Piccinelli, M. et al. "A Framework for geometric analysis of vascular structures: application to cerebral aneurysms" IEEE Transactions on Medical Imaging, 2009, 28(8), 1141-1155).

The difference between the nominal length of the stent (6) and its final length (8) corresponds to the change in length of the stent when this is positioned in the specific vessel of the patient and in the desired initial position (27).

An additional advantage of the method of the present invention is that it makes it possible to identify the regions in which the stent is not fully joined to the walls of the vessel (35). This identification can be performed by verifying that the radius of the stent is too small for the local morphology of the vessel. Such regions may present a risk of causing the migration of the device.

The method of the present invention can be carried out with the aid of one or more computer programs, i.e. as a computer-implemented method.

In a preferred embodiment the method of the present invention is used in the medical or veterinary field for predicting the length of stents when said stents are positioned inside living bodies.

EXAMPLES

Example 1

Experimental determination of the indicator ratio of the change in length of a braided stent (Silk flow diverter stent, Balt Extrusion, France) of constant radius as a function of the radius of the vascular structure.

Table 1 below shows the behaviour of the change in length of said stent with respect to the radius of the vascular structure. For this purpose, various values of the vessel radius were fixed and said change in length was determined.

TABLE 1

|  | Radius [mm] | Length [mm] | % change in length of |
|---|---|---|---|
| Nominal | 2.25 | 24.00 | 0 |
|  | 2.10 | 24.90 | 4 |
|  | 2.00 | 25.50 | 6 |
|  | 1.75 | 26.80 | 12 |

As may be observed in table 1, the stent possesses a nominal length of 24.00 mm when it has its nominal radius (2.25 mm). As the radius of the vascular structure reduces, the stent increases its length linearly, expressed as a percentage of the change in relation to its nominal length. Therefore, the behaviour of the final length of the stent can be fitted to a linear equation by means of any statistical program known in the art.

Example 2

Experimental determination of the indicator ratio of the change in length of a braided stent (Silk flow diverter stent, Balt Extrusion, France) of constant radius as a function of the perimeter of the cross section of the vessel.

Table 2 below shows the behaviour of the change in length of said stent with respect to the perimeter of the cross section of the vessel. For this purpose, various values of the vessel perimeter were fixed and said change in length was determined.

TABLE 2

|  | Perimeter [mm] | Length [mm] | % change in length of |
|---|---|---|---|
| Nominal | 14.00 | 24.00 | 0 |
|  | 11.00 | 24.90 | 4 |
|  | 8.00 | 25.80 | 8 |
|  | 5.00 | 26.80 | 12 |

As may be observed in table 2, the stent possesses a nominal length of 24.00 mm when it has its nominal perimeter (2.25 mm). As the perimeter of the vascular structure reduces, the stent increases its length linearly, expressed as a percentage of the change in relation to its nominal length. Therefore, the behaviour of the final length of the stent can be fitted to a linear equation by means of any statistical program known in the art.

Example 3

Experimental determination of the indicator ratio of the change in length of a braided stent (Silk flow diverter stent, Balt Extrusion, France) of constant radius as a function of the perimeter and the area of the cross section of the vessel.

TABLE 3

|  |  | Cross sectional area [mm$^2$] | | | |
|---|---|---|---|---|---|
|  |  | 14.00 | 10.00 | 6.00 | 2.00 |
| Perimeter [mm] | 14.00 | 0 | 5 | 8 | 12 |
|  | 11.00 | 18 | 23 | 45 | 49 |
|  | 8.00 | 30 | 42 | 59 | 70 |
|  | 5.00 | 34 | 53 | 78 | 100 |

As may be observed in table 3, in this case it is necessary to fix two descriptor parameters of the vascular structure (cross sectional area and perimeter) to obtain the percentage of the change in length of the stent in relation to its nominal length. Therefore, the behaviour of the final length of the stent can be fitted to a surface equation by means of any statistical program known in the art.

Example 4

Experimental determination of the indicator ratio of the change in length of an unbraided stent (laser-cut Enterprise stent, Cordis, United States) of constant radius as a function of the radius of the vascular structure.

Table 4 below shows the behaviour of the change in length of the laser-cut Enterprise stent (Cordis, United States) with respect to the radius of the vascular structure. For this purpose, various values of the vessel radius were fixed and said change in length was determined.

TABLE 4

|  | Radius [mm] | % change in length |
|---|---|---|
| Nominal | 2.25 | 0 |
|  | 2.00 | 2 |
|  | 1.75 | 5 |
|  | 1.50 | 7 |

As may be observed in table 4, as the radius of the vascular structure reduces, the stent increases its length linearly, expressed as a percentage of the change in relation to its nominal length. Therefore, the behaviour of the final length of the stent can be fitted to a linear equation by means of any statistical program known in the art.

Example 5

Experimental determination of the indicator ratio of the change in length of an unbraided stent (CoreValve stent, Medtronic, United States) of variable radius as a function of the radius of the vascular structure.

TABLE 5

|  | Radius [mm] | % change in length of |
|---|---|---|
| Nominal | 22.50 | 0 |
|  | 21.00 | 3 |
|  | 20.00 | 5 |
|  | 17.50 | 8 |
| Nominal | 25.00 | 0 |
|  | 23.50 | 4 |
|  | 22.50 | 6 |
|  | 20.00 | 9 |
| Nominal | 27.50 | 0 |
|  | 26.00 | 4 |
|  | 25.00 | 6 |
|  | 22.50 | 9 |

As may be observed in table 5, this experiment was carried out for each of the nominal radii of the stent (CoreValve, Medtronic, United States), as this is a stent with variable nominal radius. The method for obtaining the final length of the stent is performed in the same way as in Example 1, using any statistical program known in the art.

Example 6

Obtainment of the morphological descriptors from a three-dimensional image of a vascular structure.

From a three-dimensional image made with Integris Allura System (Philips Healthcare, Best, Netherlands) equipment of a vascular structure of the intracranial sector of the right internal carotid artery, a centreline was obtained using the Vascular Modelling Toolkit (VMTK) program and the morphological parameters shown in table 6 were obtained, such as the maximum inscribed sphere radius, curvature, torsion, cross sectional area, average radius, maximum radius, minimum radius, perimeter of the cross section, among others for each value of longitudinal position on said centreline.

From said morphological parameters shown in table 6, a statistical program known in the art may be used, which makes it possible to obtain a ratio between one or more morphological parameters of interest and the position in the vascular structure.

TABLE 6

| Maximum inscribed sphere radius | Longitudinal position | Curvature | Torsion | Cross sectional area | Average radius | Maximum radius | Minimum radius | Ratio maximum radius/minimum radius | Maximum diameter | Perimeter of cross section |
|---|---|---|---|---|---|---|---|---|---|---|
| 1.907 | 0 | 0 | −0.98692 | 12.544 | 2.0331 | 2.1489 | 1.9173 | 0.89224 | 4.077 | 12.582 |
| 1.8885 | 4.1613 | −0.054136 | −0.9926 | 12.459 | 2.0429 | 2.2002 | 1.8856 | 0.85701 | 4.1166 | 12.568 |
| 2.0107 | 8.3226 | −0.030178 | −0.93702 | 13.862 | 2.1302 | 2.2531 | 2.0073 | 0.89089 | 4.3097 | 13.234 |
| 1.8674 | 12.484 | −0.027985 | −0.95578 | 13.535 | 2.0805 | 2.2121 | 1.9489 | 0.88101 | 4.3617 | 13.085 |
| 1.8438 | 16.645 | −0.5923 | −0.40477 | 14.207 | 2.28195 | 2.7253 | 1.8386 | 0.67464 | 4.6833 | 13.61 |
| 1.9457 | 20.806 | −0.53432 | 0.52435 | 15.79 | 2.3631 | 2.7497 | 1.9765 | 0.71879 | 5.136 | 14.457 |
| 2.0707 | 24.968 | −0.63991 | 0.34557 | 17.77 | 2.3689 | 2.6672 | 2.0706 | 0.77634 | 5.2391 | 15.12 |
| 2.0153 | 29.129 | −0.89548 | −0.29934 | 14.594 | 2.20295 | 2.3833 | 2.0226 | 0.84865 | 4.5438 | 13.598 |
| 1.8972 | 33.29 | −0.57898 | −0.5222 | 12.779 | 2.0677 | 2.2424 | 1.893 | 0.84419 | 4.1766 | 12.784 |
| 1.5763 | 37.452 | −0.32849 | −0.39932 | 9.2959 | 1.737 | 1.9017 | 1.5723 | 0.82677 | 3.6891 | 10.889 |
| 1.3678 | 41.613 | −0.10886 | −0.77779 | 6.1342 | 1.41025 | 1.4624 | 1.3581 | 0.9287 | 2.8914 | 8.8058 |
| 1.7278 | 45.774 | 0.28487 | −0.93102 | 10.492 | 1.87065 | 2.0174 | 1.7239 | 0.8545 | 3.8766 | 11.533 |
| 1.5611 | 49.936 | 0.54803 | −0.81345 | 25.222 | 4.8383 | 8.1138 | 1.5628 | 0.19261 | 9.731 | 22.377 |
| 1.2947 | 54.097 | 0.42801 | −0.61848 | 5.6763 | 1.38435 | 1.4817 | 1.287 | 0.86858 | 2.824 | 8.4755 |
| 1.1914 | 58.258 | 0.16155 | −0.0832 | 4.9142 | 1.27965 | 1.3798 | 1.1795 | 0.85481 | 2.6303 | 7.8947 |
| 1.2817 | 62.42 | −0.10941 | 0.20061 | 65.069 | 6.6057 | 11.946 | 1.2654 | 0.10593 | 13.277 | 34.624 |
| 0.95329 | 66.581 | 0.86878 | 0.21637 | 3.7863 | 1.32709 | 1.6987 | 0.95548 | 0.56247 | 2.7613 | 7.3283 |
| 1.134 | 70.742 | 0.3084 | 0.14386 | 4.4387 | 1.20455 | 1.2836 | 1.1255 | 0.87683 | 2.468 | 7.5022 |
| 1.0901 | 74.903 | −0.22175 | 0.40717 | 3.8834 | 1.13415 | 1.1875 | 1.0808 | 0.91014 | 2.2933 | 7.0125 |
| 1.0026 | 79.065 | −0.22181 | 0.56237 | 3.3605 | 1.04708 | 1.1042 | 0.98996 | 0.89657 | 2.1872 | 6.5298 |
| 0.86925 | 83.226 | −0.50415 | 0.281 | 2.6138 | 0.924065 | 0.98242 | 0.86571 | 0.8812 | 1.9138 | 5.758 |
| 0.78943 | 87.387 | −0.68281 | −0.50576 | 2.5245 | 0.909895 | 1.0446 | 0.77519 | 0.74209 | 1.48E−76 | 1.71E−264 |

Example 7

Use of the method of the present invention for calculating the actual final length of a braided stent (Silk flow diverter stent, Balt Extrusion, France).

Figure 9:
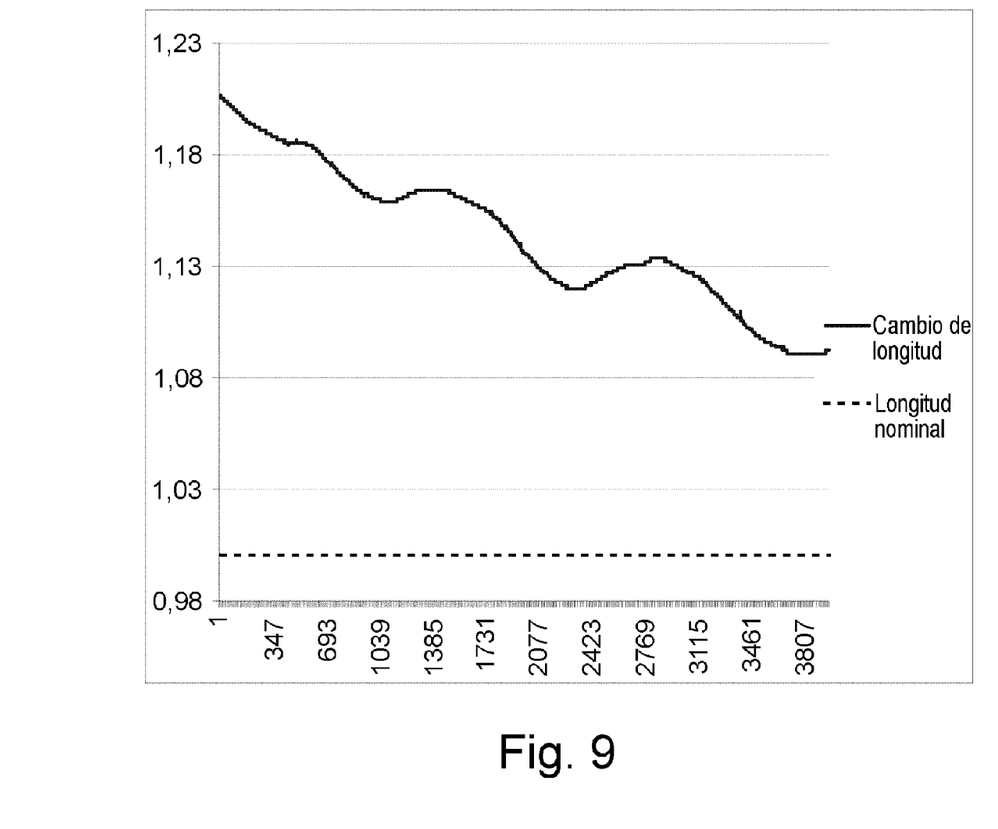
FIG. 9 shows the change in length of an actual stent calculated according to the method of the present invention, compared to the nominal length of said stent.

The final length of the stent used in example 1 was calculated according to the actual geometry of a vascular structure in which said stent was to be implanted. Throughout the length of the vascular structure the ratio of the change in length of said stent was up to 1.2 times its nominal length. The results are shown in FIG. 9.

What is claimed is:

1. A method for determining the final length of a stent before it is positioned in a vascular structure which comprises:
   a) obtaining an angiographic three-dimensional image of the vascular structure in which the stent will be positioned, and tracing, by a computer, a centreline of said vascular structure in the three-dimensional image, defining the exact location of the an initial point at which said stent will be positioned and dividing said centreline of the vascular structure into small segments;
   b) measuring, by the computer, on the three-dimensional image descriptor parameters of a morphology of said vascular structure for a first segment which starts from said initial point at which said stent will be positioned in said vascular structure;
   c) calculating, by the computer, a length of the stent for said first segment using an indicator ratio of the change in length of the stent as a function of a local morphology of the vascular structure;
   d) subtracting, by the computer, said length of the segment calculated in step c) from the nominal length of the stent to obtain a new nominal length; if said new nominal length is different from 0 then steps b) to d) will be repeated for the segment contiguous with the preceding segment; if the new nominal length is 0, all the distances of each segment will be added together, and this sum will be the final length of said stent after positioning.

2. The method, according to claim 1, wherein said indicator ratio of the change in length of the stent is obtained experimentally.

3. The method, according to claim 1, wherein said indicator ratio of the change in length of the stent is obtained by mathematical modelling.

4. The method, according to claim 1, wherein said descriptor parameters of a vascular morphology are an average radius, maximum inscribed sphere radius, cross sectional area, perimeter of a cross section, minimum radius of the cross section, maximum radius of the cross section, curvature/torsion or any combination of these.

5. The method, according to claim 1, wherein said indicator ratio of the change in length of the stent is given by the manufacturer of said stent.

\* \* \* \* \*